(12) United States Patent
Yanof et al.

(10) Patent No.: US 6,366,796 B1
(45) Date of Patent: Apr. 2, 2002

(54) METHOD AND APPARATUS FOR PLANNING BRACHYTHERAPY SURGICAL PROCEDURES

(75) Inventors: Jeffrey M. Yanof, Solon; Kenneth L. Freeman, Stow, both of OH (US); Barry L. Werner, Chesterbrook, PA (US)

(73) Assignee: Philips Medical Systems (Cleveland), Inc., Highland Heights, OH (US)

( * ) Notice: Subject to any disclaimer, the term of this patent is extended or adjusted under 35 U.S.C. 154(b) by 0 days.

(21) Appl. No.: 09/426,929

(22) Filed: Oct. 22, 1999

Related U.S. Application Data

(60) Provisional application No. 60/105,422, filed on Oct. 23, 1998.

(51) Int. Cl.[7] .................................................. A61B 5/05
(52) U.S. Cl. ...................... 600/407; 600/410; 600/411; 600/425; 600/427; 600/437; 600/439; 378/21
(58) Field of Search ................................. 600/427, 407, 600/409, 410, 416, 417, 423, 424, 425, 437, 443, 459, 462, 461, 411, 429; 606/130; 378/21

(56) References Cited

U.S. PATENT DOCUMENTS 6,129,670 A * 10/2000 Burdette et al. ............ 600/427

FOREIGN PATENT DOCUMENTS

| EP | 469 966 | 2/1992 |
|----|---------|--------|
| EP | 676 178 | 10/1995 |
| FR | 2660185 | 10/1991 |
| FR | 2692466 | 12/1993 |
| WO | WO 96 14880 | 5/1996 |
| WO | WO 98 23213 | 6/1998 |
| WO | WO 98 23214 | 6/1998 |

* cited by examiner

Primary Examiner—Marvin M. Lateef
Assistant Examiner—Jeoyuh Lin
(74) Attorney, Agent, or Firm—Fay, Sharpe, Fagan, Minnich & McKee LLP

(57) ABSTRACT

A tomographic scanner includes an imaging device for obtaining images of the anatomy of a patient. A localizer device such as an articulated arm includes a base portion mounted in a fixed relationship to the imaging device and a free end adapted for selective movement into varied positions near a patient body disposed on the imaging device. A guide device such as grid lattice is attached to the free end of the arm. A position transducer associated with the localizer device generates information as to the position of the localizer and hence the position of the guide device in scanner coordinates. The guide device contains a plurality of needle guides. The position of the guide device is displayed in relation to images of the anatomy of the patient. This information is used by the operator to guide the insertion of brachytherapy seeds in a desired pattern and location in relation to the anatomy of the patient.

18 Claims, 5 Drawing Sheets

METHOD AND APPARATUS FOR PLANNING BRACHYTHERAPY SURGICAL PROCEDURES

CROSS-REFERENCE TO RELATED APPLICATIONS

This application claims the benefit of U.S. Provisional Application No. 60/105,422, filed Oct. 23, 1998. This application relates to U.S. Application Ser. No. 08/980,337, filed Nov. 28, 1997.

BACKGROUND OF THE INVENTION

The present invention relates to the art of interactive image-guided surgery. It finds particular application in the field of brachytherapy of the prostate and will be described in particular reference thereto. It is to be appreciated, however, that the invention is also applicable to a wide range of imaging equipment and minimally invasive stereotactic and other surgical procedures including, for example, cryogenics, photo-activation concepts, other local cancer treatments, and the like.

Brachytherapy is a form of radiation therapy in which radioactive seeds are inserted into cancerous tissue, thereby attacking cancer cells. It is desirable that the seeds be distributed within the malignant tissue in a particular selected pattern. It is generally desirable that the seeds be distributed evenly so as to avoid hot (e.g., over-radiated), and cold (e.g., under-radiated) spots. Additionally, the seeds should not be placed outside of the target region.

One method for inserting the seeds in the case of prostate brachytherapy involves trans-rectal ultrasound image guidance. One disadvantage of such a procedure is that it is uncomfortable for the patient. Yet another disadvantage is that preoperative planning and visualization information is limited.

There is a need, therefore, to provide a brachytherapy planning method and apparatus that enables non-invasive preoperation planning using visualization information showing a patient's anatomy together with one or more planning trajectories.

Preferably, the planning method and apparatus includes a localizing device for determining a position of a surgical guide device relative to the visualization information. In that way, an interventionist can move the localizing device and surgical guide device into a range of positions relative to a patient so that multiple views of a range of planning trajectories are shown on a display together with a virtual representation of the patient's anatomy.

SUMMARY OF THE INVENTION

In accordance with the present invention, a method of non-invasive planning a brachytherapy surgically procedure on an area of a patient is provided. A volumetric image data set of an area of the patient to be treated is provided. A multi-apertured surgical planning guide device is disposed in a first position adjacent the patient to be treated. The volumetric image data set of the area of the patient is displayed on a display device with a virtual representation of the guide lattice device superimposed on the volumetric image data set to provide a visual indication of a position of the guide lattice relative to anatomy of the patient.

In accordance with a more detailed aspect of the planning method of the invention, multiple planar portions of the volumetric image data set are displayed on the display device simultaneously. A first planar portion of the volumetric image data set is coplanar with a major plane of the guide lattice device and corresponds to a physical position of the guide lattice device relative to the area of the patient. A second planar portion of the volumetric image data set is orthogonal with the major plane of the guide lattice and corresponds to a first cross-sectional view of the area of the patient with a first cross-sectional virtual representation of the guide lattice superimposed on the volumetric image data set. A third planar portion of the volumetric image data set is orthogonal with the major plane of the guide lattice and also orthogonal with the second planar portion. The third planar portion corresponds to a second cross-sectional view of the area of the patient with a second cross-sectional virtual representation of the guide lattice device superimposed on the volumetric image data set.

In accordance with a further more limited aspect of the method in accordance with the present invention, the step of providing the volumetric image data set of the area of the patient to be treated includes retrieving the data set from a data storage device such as a computer memory. In a more limited aspect, the step of providing the volumetric image data includes scanning the area of the patient using an imaging device to generate the volumetric image data set.

Still further in accordance with the invention, a first virtual needle linear planning trajectory is defined extending through the volumetric image data set from a first aperture of the multi-apertured surgical planning guide lattice device to a first virtual needle end point in the volumetric image data set. The first virtual needle linear planning trajectory is displayed on the display device. The length of the first virtual needle linear planning trajectory is selectively adjustable to extend through the volumetric image data set from the guide lattice device to a second virtual needle end point in the volumetric image data set.

Still further in accordance with the present invention, an apparatus is provided for planning a surgical procedure for inserting a plurality of objects into a patient along a plurality of surgical planning trajectories from a plurality of entry points on the patient to a plurality of target points within the patient. The apparatus includes a first device storing an image volume data set of an area of a patient to be treated. A multi-apertured surgical planning grid lattice is disposed in a first position relative to the patient for defining a plurality of linear planning trajectories extending from the planning grid lattice and through the patient. A display device is adapted for displaying the image volume data set of the area of the patient with a virtual representation of the grid lattice superimposed on the image volume data set to provide a visual image of a position of the grid lattice relative to anatomy of the patient. In that way, the grid can be physically centered over the target organ and then appropriately rotated or adjusted to align the virtual needles with the organ or to avoid critical structures in the patient.

In accordance with a more limited aspect of the planning apparatus of the present invention, the first device is preferably an imaging device adapted to scan the area of the patient to be treated to generate the image volume data set.

Still further, the apparatus for planning the surgical procedure includes a localizing means for determining a position of the grid lattice relative to the image volume data set. The display device is responsive to the localizing means for displaying the image volume data set of the area of the patient with the virtual representation of the grid lattice superimposed on the image volume data set to provide the visual representation of the position of the grid lattice relative to the anatomy of the patient.

One advantage of the present invention is that a method and apparatus are provided for planning brachytherapy surgical procedures as well as other minimally invasive surgical procedures including cryogenics, photo-activation concepts, other local cancer treatments, stereotactic procedures, and the like.

Another benefit of the invention derives from the ability of interventionists or brachytherapists to create and visualize a plurality of surgical planning trajectories into the patient relative to anatomy of the patient so that a plurality of radioactive seeds or other devices can be placed within the patient at a plurality of preselected target points.

Still other advantages and benefits of the invention will become apparent to those skilled in the art upon a reading and understanding the following detailed description.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof, and wherein.

DETAILED DESCRIPTION OF THE PREFERRED EMBODIMENT

Figure 1:
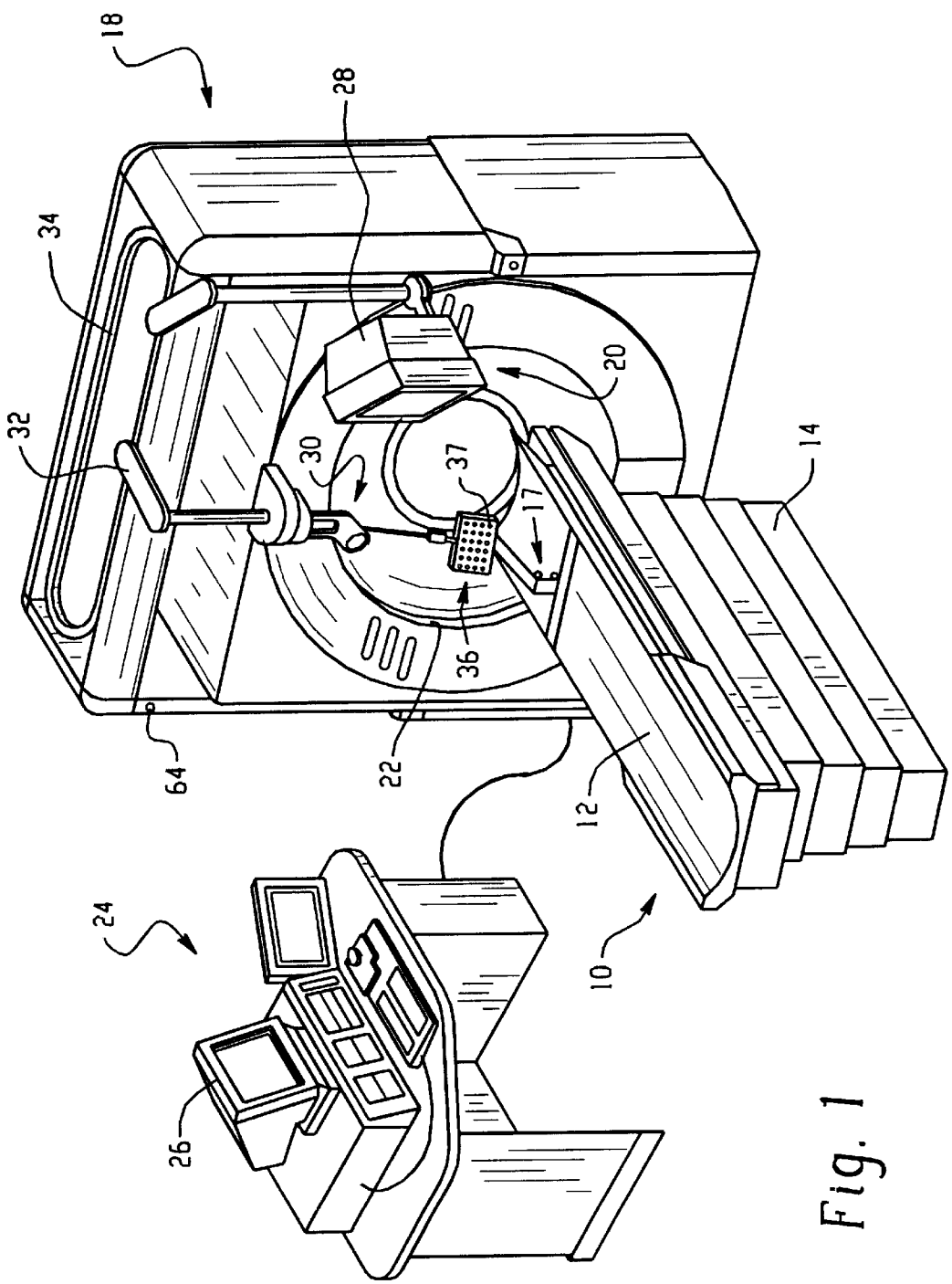
FIG. 1 is a diagrammatic illustration of a frameless stereotactic scanner system including a localizing device in the preferred form of an arm apparatus for image guiding surgical instruments in accordance with the preferred embodiment of the present invention.

Referring now to the drawings wherein the showings are for the purposes of illustrating the preferred embodiments of the invention only and not for purposes of limiting same, with reference first to FIG. 1, a patient table or support 10 includes a patient supporting surface 12 that is mounted for longitudinal movement relative to a base portion 14. The base portion 14 includes a motor for raising and lowering the patient support surface 12 and for moving the patient support surface longitudinally. Position encoders are also provided for generating electrical signals indicative of the height and longitudinal position of the patient support. An adjustable support structure 17 is mounted to the patient support.

A diagnostic imaging apparatus 18, preferably a volumetric imaging apparatus, is disposed in axial alignment with the patient table such that a patient or subject on the patient support surface 12 can be moved into and through a bore 20 of the volumetric imager. In the illustrated embodiment, the volumetric imager is a CT scanner which includes an X-ray tube mounted for repeated circular travel within a preselected plane. The X-ray tube projects a fan-shaped beam of radiation through a ring 22 of radiation translucent material, through the patient support 12, through a region of interest of the subject, and to a ring or arc of radiation detectors positioned opposite the X-ray tube. As the X-ray tube rotates within the plane, a series of data lines are generated, which data lines are reconstructed into at least a slice image by a reconstruction processor included in a control console 24. The control console is typically remotely located in a shielded room adjacent the scan room. More specifically to the preferred embodiment, the patient support 12 moves longitudinally as the X-ray tube is rotating around the subject such that a selected volume of the patient is scanned along a spiral path or a series of slices. The position of the X-ray tube is monitored by a rotational position encoder, and the longitudinal position of the patient support is monitored by a longitudinal position encoder within the table 10. The reconstruction processor reconstructs a volumetric image representation from the generated data lines. The control console 24 typically includes one or more monitors 26 and various standard operator input devices such as a keyboard, trackball, mouse, or the like. An interventionist control console 28 is supported from overhead on a track atop the CT scanner.

A localizing device in the preferred form of a mechanical frameless stereotactic arm assembly 30 is supported from overhead by a carriage 32 movable on an oval track system 34 affixed to the top of the volumetric diagnostic imaging apparatus 18 as generally shown. The carriage is preferably lockable in one or more predetermined fixed locations on the oval track so that a minimally invasive surgical instrument 36 carried thereon can be positioned in monitored positions and orientations by an interventionist in preparation for (preoperative planning and visualization) and in carrying out a surgical procedure. Preferably, the plurality of instruments 36 may be interchangeably mounted on the arm assembly 30.

Figure 3:
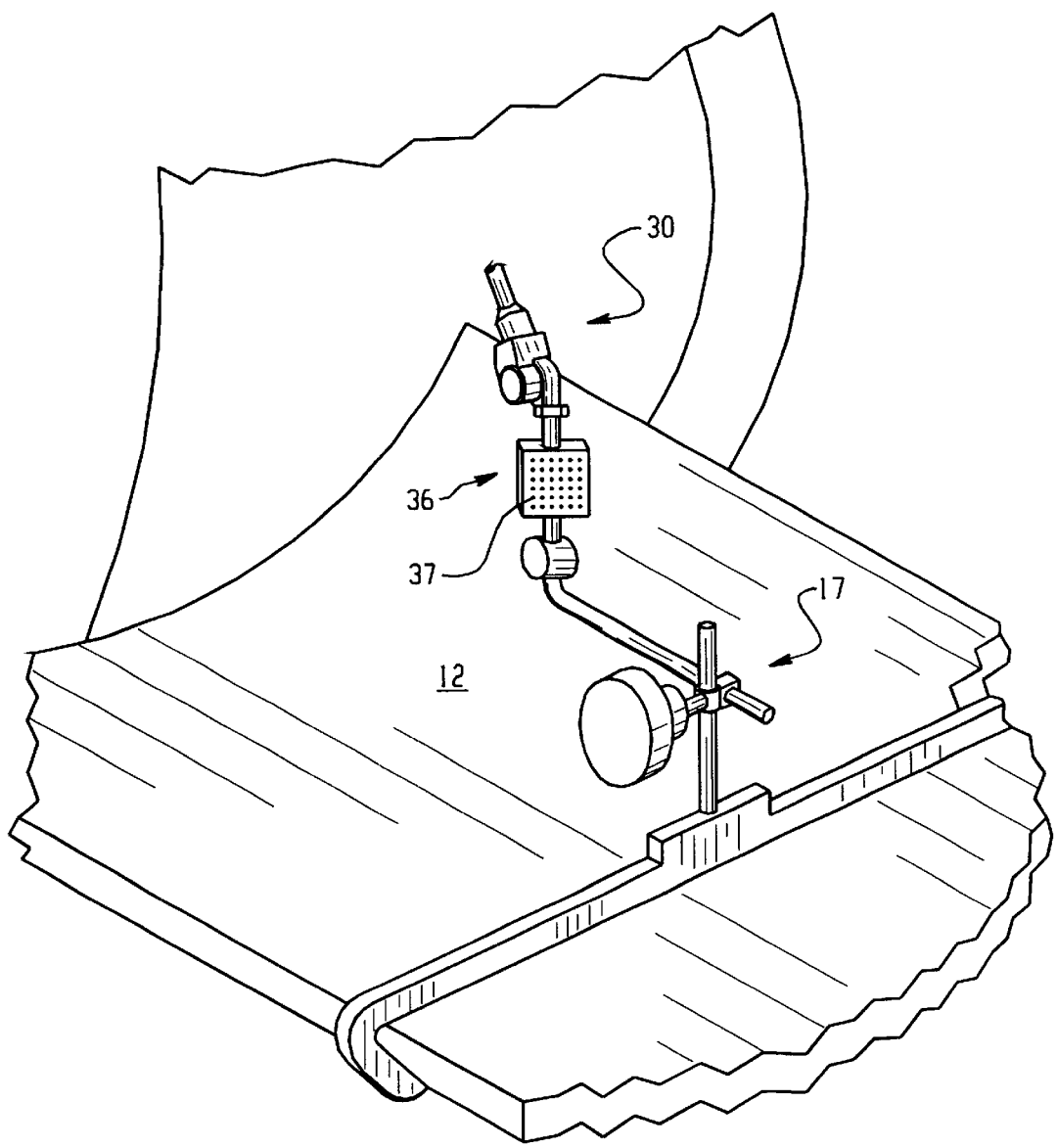
FIG. 3 is a detailed view of a mechanical arm, guide lattice, and supplemental support; and, FIG. 4 is a diagrammatic illustration of the planning image processing performed with the apparatus of FIG. 1.

With continued reference to FIG. 1 and further reference to FIG. 3, the surgical instrument 36 of the preferred embodiment is a guidance device known as a grid lattice. The grid lattice 36 includes a two-dimensional array of spaced apart through apertures 37 which serve as needle guides. In particular, needles used in brachytherapy are selectively inserted in one or more of the apertures such that the needle is guided thereby. In a preferred embodiment, the grid lattice is approximately 3 cm×3 cm and carries a regular array of needle guides spaced at 0.5 cm intervals.

Overall, the position and orientation of the grid lattice is determined by the position of a localizing device. In the preferred embodiment of the invention shown, the localizing device is a mechanical arm assembly 30. The location of the mechanical arm assembly 30, the relative position of each arm joint, and the position of the carriage 32 on the oval track system 34 in the scanner coordinate system are used to determine the position and orientation of the grid lattice relative to the image volume data set and relative to the patient to be described below.

Figure 2:
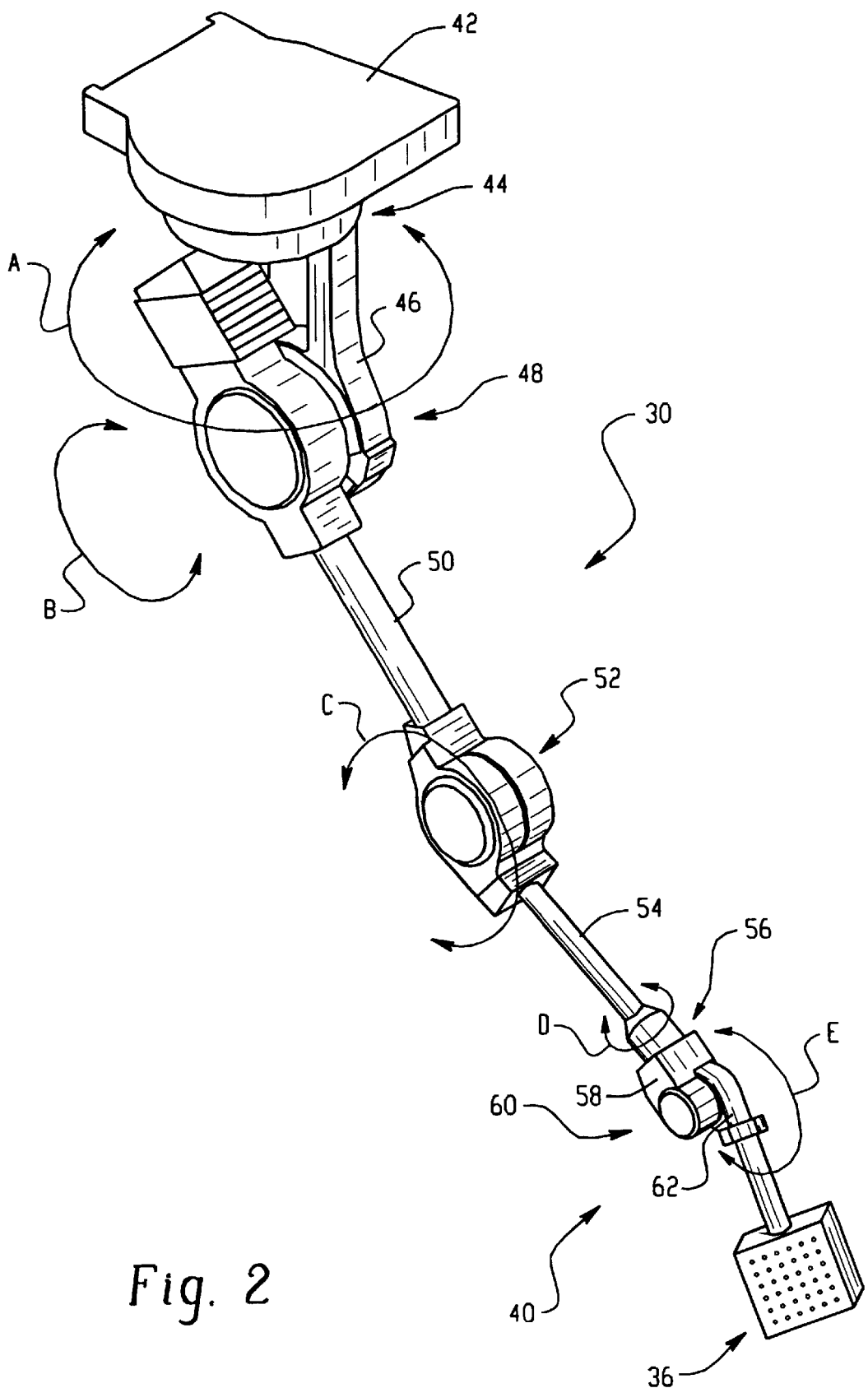
FIG. 2 is a perspective view of the frameless mechanical arm assembly carrying a guidance device formed in accordance with the present invention.

The articulated arm assembly 30 is shown generally in FIG. 2 and includes a plurality of arm segments which are interconnected by pivot members forming joints between the arm segments. In that way, a free end 40 of the arm is selectively movable in multiple orientations as necessary to position the grid lattice 36 into various desired positions over the patient support 12 and relative to the patient. A base member 42 is rigidly connected to the carriage 32 using suitable fasteners, epoxies, or the like. A base joint 44 permits rotation of a primary support member 46 in a direction marked A. Similarly, from the immovable base end of the arm, a shoulder joint 48 permits rotation of an upper arm member 50 in a direction marked B, an elbow joint 52 permits rotation of a lower arm member 54 in a direction marked C, a forearm joint 56 permits rotation of a knuckle member 58 in a direction marked D, and, lastly, a wrist joint 60 permits rotation of a wrist member 62 in a direction marked E.

At least one position resolver, preferably an optical incremental encoder, is provided at each joint of the mechanical arm assembly 30 to monitor incremental movement and rotation of the arms relative to each other for reasons that will subsequently become apparent. The optical incremental encoders generate feedback pulses indicative of the relative angular and rotational position of the various arm members with respect to each other in a well-known manner. The feedback pulses are carried back to an imaging apparatus control circuit using suitable wires or flexible shielded cables extending through the multiple members of the arm assembly. In that way, the position and orientation of the wrist member 62 with respect to the imaging apparatus reference frame and the volumetric image representation obtained by the imaging apparatus can be determined.

The physical dimensions and other parameters of the guide lattice 36 are known a priori. Preferably, the guide lattice 36 provides a unique identification signal to the system. The identification signal is used by the imaging apparatus control circuit to index a look up table for retrieving various physical dimensional and other functional parameters corresponding to the guide lattice 36. In this manner, the physical dimensions and other functional parameters, together with the mechanical interconnection which is measured by the resolvers and/or encoders, provides an accurate indication of the position and orientation of the guide lattice 36 relative to the CT scanner and, hence, relative to the image acquired by the CT scanner imaging device.

Figure 4:
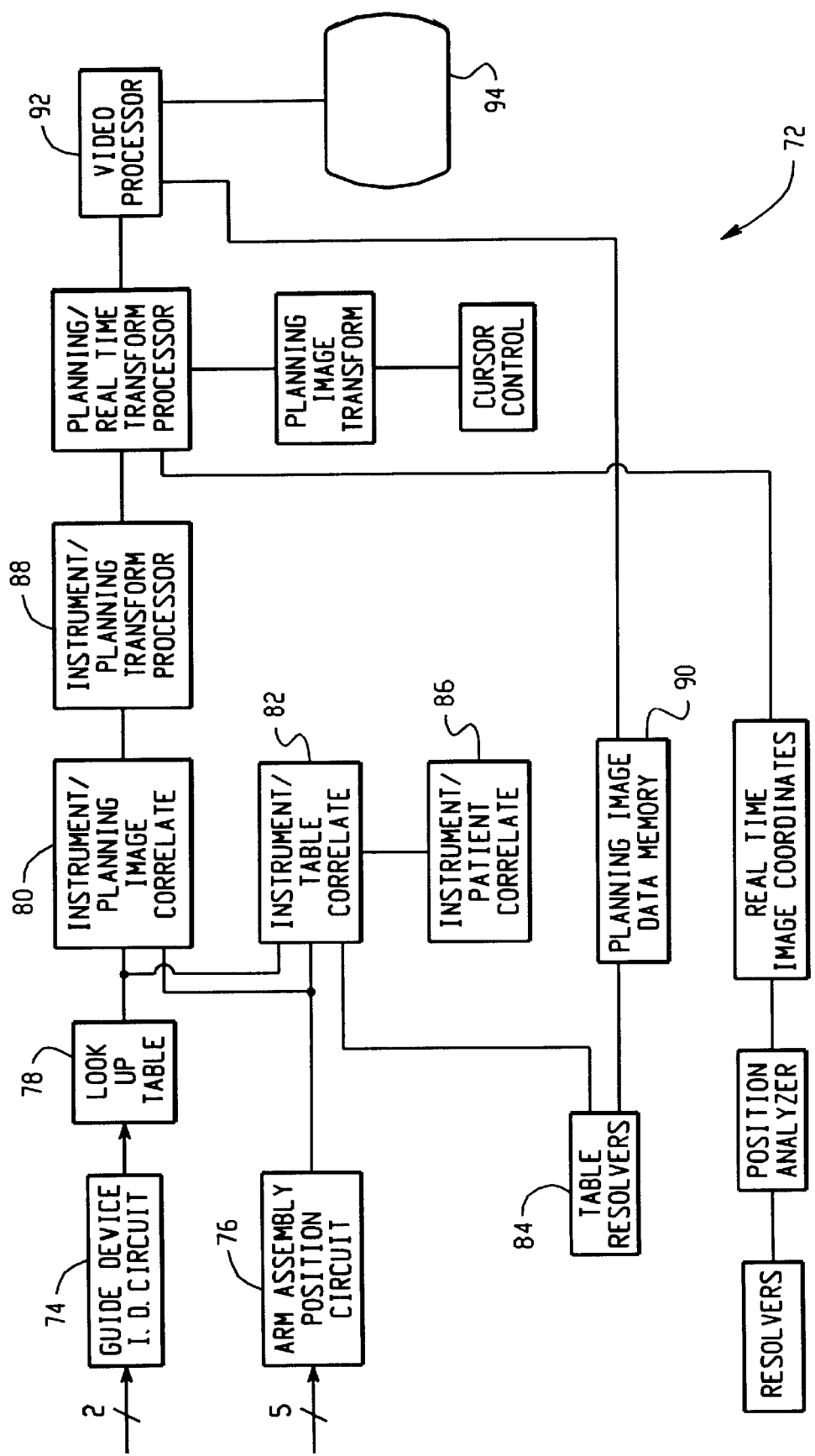

With reference now to FIG. 4, an instrument coordinate circuit 72 determines the position and trajectory of the guide lattice 36 in instrument space, preferably in a coordinate system of the guide lattice 36. The instrument coordinate system circuit includes a guidance device identification circuit 74 and a mechanical arm assembly position circuit 76. The guidance device identification circuit 74 receives the device identification signal from the guide 36 lattice and indexes a look up table 78 to retrieve dimensional and functional information. The mechanical arm assembly position circuit 76 is connected with the incremental resolvers on the mechanical arm assembly 30 to receive signals indicative of changes of position and orientation of the mechanical arm in instrument space. An instrument-planning scanner correlating processor 80 determining the correlation or transform between the guide lattice 36 and the volumetric scanner 18 coordinate systems. The correlation or transform is normally described in terms of three-dimensional offset, angular offset or rotation, and scaling.

Using analogous mathematics or known mechanical relationships as above, a device to patient table correlating processor 82 determines the correlation or transform between the patient table and the surgical instrument.

Table resolvers 84 located in the patient table contribute vertical and longitudinal offsets to the correlation between the guide lattice and the patient table when the table is raised or lowered and when the patient support 12 is moved axially. An instrument to patient correlation processor 86 determines a correlation between the guide lattice system and a patient coordinate system. This may be done to provide reassurance to an interventionist by placing the surgical instrument on three or more known reference points on the patient. Such points might include readily identifiable anatomical structures such as the tip of the nose, distinctive points of bones, fiducial markers that are placed during the volumetric imaging process, or the like.

The equations for patient support movement are as follows: Let the distance of the first image (i.e., reference image, maximum z value along the patient support) from the aperture (z-0 in scanner coordinates) along the z-axis be represented by:

$$D_{max\ z\ image\ from\ aperture} = (P[z]_{max\ z\ image\ pt\ support} - P[z]_{present\ pt\ support}).$$

Then the equation for the transformations for patient support movements are as follows:

$$\text{Localizer Tip}[z] = \text{Localizer Tip}_{scanner\ coord}[z] - D_{max\ z\ image\ from\ aperture}$$

where P[z] is the patient support position in the z axis. A similar equation can be written for the patient support movements along the y axis.

If the reference image is in the aperture, then $$D_{max\ z\ image\ from\ aperture} = 0$$

and $$\text{Localizer Tip}[z] = \text{Localizer Tip}_{scanner\ coord}[Z]$$

Thus, if the localizer has a z value in scanner coordinates which is the same as the reference image, then $$D_{max\ z\ image\ from\ aperture} = \text{Localizer Tip}_{scanner\ coord}[Z]$$

and $$\text{Localizer Tipt}[z] = 0$$

which is the z-axis origin of the image space.

Patient restraint mechanisms (not shown) can be used in order to prevent gross movements of the patient relative to the patient support.

An instrument to volumetric image coordinate system transform processor 88 receives the correlation or transform from the guide lattice 36 to the planning image processor 80. The instrument to volumetric image processor operates on input position and orientation coordinates in image space to transform them into volumetric image data space and vice versa. Knowing the position of the guide lattice in volumetric or planning data space enables the guide position and orientation to be superimposed on the volumetric planning image data.

During a medical procedure, the patient is positioned in the volumetric planning scanner and a volumetric image is generated. The volumetric image is stored in a volumetric or planning data memory 90. The position of the patient table during the generation of the planning data, particularly as the table moves to generate spiral or slice data, is stored in conjunction with the volumetric planning data such that the data is correlated with the patient table coordinate system. The operator control console 24 controls the volume planning image data memory or a video processor 92 such that the selected slices, projection images, surface renderings, or other conventional displays of the data are generated for display on a planning image display 94. Preferably, the planning image display includes corresponding sagittal, coronal, and axial slices.

Because the planning image display is generated before the surgical procedure, the planning movement of the surgical instrument is preferably displayed in the planning image coordinate system on the interventionist control console 28. The coordinates and trajectory of the surgical instrument are conveyed by the instrument to planning image transform processor 88 for conversion into the planning image coordinate system. The location and trajectory of the surgical instrument in the planning image coordinate system is communicated to the video processor 92 which superimposes the lattice position and trajectory on the CT data display.

More specifically, FIG. 5 shows multiple different views of the position and orientation of the guide lattice superimposed on the volumetric image data so as to provide the operator with an indication of the position of the guide lattice in relation to the anatomy of the patient. In one embodiment, the four views of FIGS. 5A–D are displayed simultaneously on the operator console 26. As the position of the physical guide lattice is varied, the position of the guide in relation to the image data is updated accordingly.

Figure 5A:
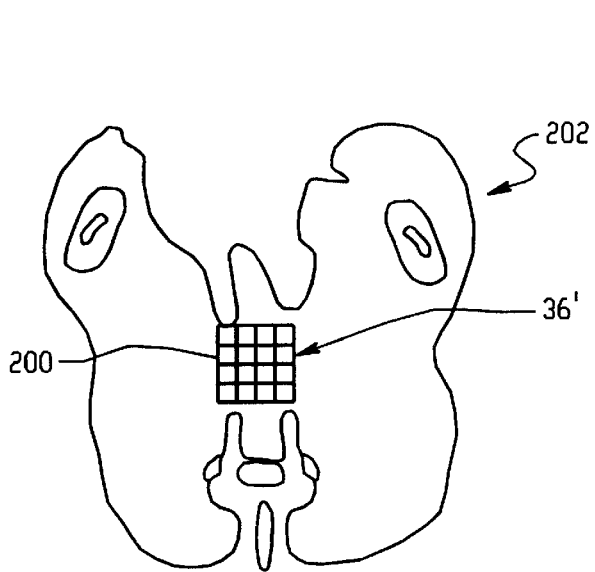
FIGS. 5A–5D depict visual displays of the grid lattice superimposed on volumetric image data.
Figure 5B:
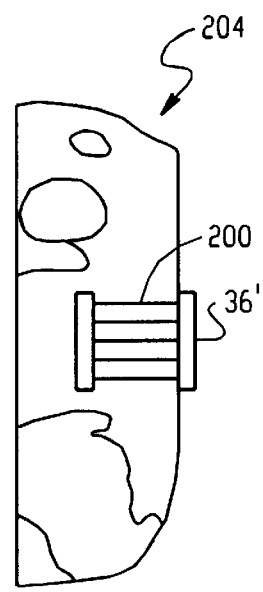
Figure 5C:
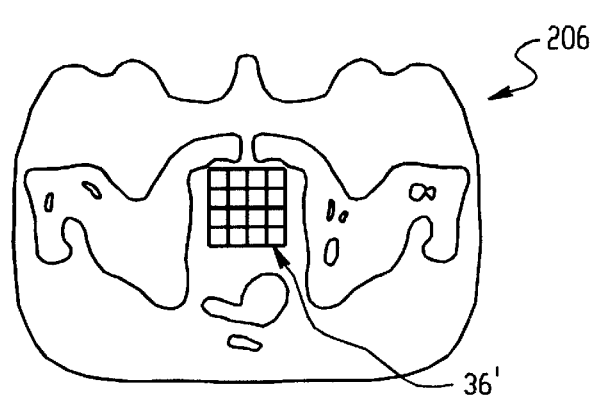

With particular reference to FIGS. 5A and 5C, the image data is displayed in a plane coplanar with the major plane of the guide lattice with the grid 36 superimposed thereon. In FIG. 5A, a planar portion 202 of the image data is displayed at a reference or zero depth which corresponds to the physical position of the guide lattice. In procedures involving the prostate gland, this is generally a position which is in physical contact with the anatomy of the patient. In FIG. 5C, a planar portion 206 of the image data is displayed at a depth preferably corresponding the depth of a virtual needle selected by the operator via operator interface 26.

Figure 5D:
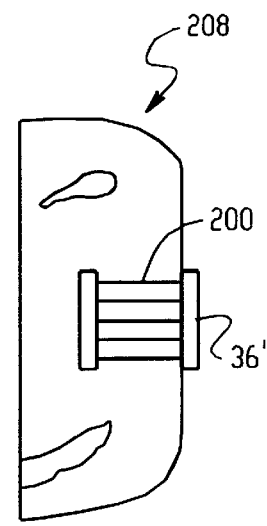

FIGS. 5B and 5D display planar portions 204, 208 that are orthogonal to the major plane of guide lattice and to each other. For example, if the guide lattice was placed in a transverse axial position, FIG. 5B would depict a coronal view, with a cross section of the lattice representing a column of "virtual needles" displayed in relation to the image data. FIG. 5D would depict a sagittal view, with a row of "virtual needles" displayed in relation to the image data. If the grid is oriented out of the transverse plane, all views would be multiplanar reformatted to represent oblique slices through the volume data set.

With continuing reference to FIGS. 5A–D, the operator can select individual apertures on the guide lattice using a device such as a joystick. A virtual needle 200 corresponding to the selected aperture may then be displayed in highlighted form, for example in a different color. The intersection of the views which are orthogonal to the grid (i.e., the views of FIGS. 5B and 5D) is at the center of the virtual needle 200. The images of FIGS. 5B, 5C, and 5D intersect at a point which corresponds to the tip of the virtual needle 200.

The depth of the virtual needle 200 is adjusted through the operator interface. As the depth of the virtual needle is adjusted, its location is shown adjusted in relation to the image data in each of the views of FIGS. 5B, 5C, and 5D. The length of the virtual needle in the depth direction is calculated by the system and is displayed on the operator interface or stored. This distance is used by the operator in setting the correct depth for insertion of the actual needle subsequent to completion of the planning process.

A plurality of virtual needles may be selected in succession. Once the location corresponding to a first aperture (and thus seed) has been determined, the process is repeated for additional apertures. As an aid to visualization, it may be desirable to display the selected location for each of the seeds on the images of FIGS. 5B, 5C, and 5D until desired location for a plurality of the seeds is determined.

In operation, the patient is imaged, and image data corresponding to the anatomy of the patient is generated. The operator then positions the guide lattice to the desired position and orientation in relation to the anatomy. When in the desired position, the guide lattice may be attached to the adjustable support structure 17. The desired needle depth is determined selecting the desired apertures and adjusting the depth of the virtual needles. In brachytherapy of the prostate gland, for example, bounding structures such as the wall of the rectum may be located and the desired depth adjusted accordingly.

Brachytherapy needles are inserted through the appropriate apertures according to a desired dose plan. The needles are inserted to the desired depth, and the seeds are deposited accordingly. Verification CT slices may then be taken to confirm the dose distribution. Preferably, the guide lattice is detached from the arm 30 and attached to the supplemental support 17 prior to the verification scan.

Optionally, the guide lattice 36 may be detached from the arm 30 after the lattice 36 has been attached to the support structure. The desired needle may then be attached to the arm 30. The actual position of the needle may then be superimposed on the image data to provide the operator with a real time indication of the position of the needle in relation to the anatomy of the patient.

The invention has been described with reference to the preferred embodiment. Obviously, modifications and alterations will occur to others upon reading and understanding the preceding description. It is intended that the invention be construed as including all such modifications and alterations insofar as they come within the scope of the appended claims or the equivalents thereof.

Having thus described the invention, it is claimed:

1. A method of planning a brachytherapy surgical procedure on an area of a patient, the method comprising the steps of:

using an imaging device, scanning an area of the patient to generate a volumetric image data set of the area of the patient;

moving a multi-apertured surgical planning guide lattice device relative to the patient and the imaging device to a first position adjacent said patient to be treated; and, displaying the volumetric image data set of said area of said patient on a display device with a virtual representation of the guide lattice device superimposed on the volumetric image data set to provide a visual indication of a position of the guide lattice device relative to anatomy of said patient.

2. The method according to claim 1 wherein the displaying step includes:

displaying a first planar portion of said volumetric image data set coplanar with a major plane of the guide lattice device, the first planar portion of the volumetric image data set corresponding to a physical position of the guide lattice device relative to said area of said patient;

displaying a second planar portion of the volumetric image data set orthogonal with said major plane of the guide lattice device, the second planar portion of the volumetric image data set corresponding to a first cross-sectional view of said area of said patient with a first cross-sectional virtual representation of the guide lattice device superimposed on the volumetric image data set; and, displaying a third planar portion of the volumetric image data set orthogonal with said major plane of the guide lattice and orthogonal with said second planar portion, the third planar portion of the volumetric image data set corresponding to a second cross-sectional view of said area of said patient with a second cross-sectional virtual representation of the guide lattice device superimposed on the volumetric image data set.

3. The method according to claim 2 wherein the step of moving the surgical planning guide lattice device includes moving the surgical planning guide lattice device independent of movement of the imaging device to a plurality of positions adjacent said patient to be treated.

4. The method according to claim 1 further including the steps of:
defining a first virtual needle linear planning trajectory extending through the volumetric image data set from a first aperture of the multi-apertured surgical planning guide lattice device to a first virtual needle end point in the volumetric image data set;
displaying said first virtual needle linear planning trajectory on said display device; and,
adjusting a length of said first virtual needle linear planning trajectory to extend through said volumetric image data set from the guide lattice device to a second virtual needle end point in the volumetric image data set.

5. The method according to claim 4 wherein the displaying step includes:
displaying a first planar portion of said volumetric image data set coplanar with a major plane of the guide lattice device, the first planar portion of the volumetric image data set corresponding to a physical position of the guide lattice relative to said area of said patient; and,
displaying a second planar portion of said volumetric image data set parallel with said major plane of the guide lattice, the second planar portion of the volumetric image data set being coincident with said position of said first virtual needle end point during said adjusting of said length of said first virtual needle planning trajectory to extend from said first virtual needle end point to said second virtual needle end point.

6. The method according to claim 4 wherein the step of defining said first virtual needle linear planning trajectory includes defining a plurality of virtual needle planning trajectories extending through said volumetric image data set from a corresponding plurality of apertures formed by said guide lattice device to a corresponding plurality of virtual needle end points in the volumetric image data set.

7. The method according to claim 6 wherein the displaying step further includes:
displaying a first planar portion of said volumetric image data set orthogonal with a major plane of said guide lattice device and collinear with a first set of said virtual needle linear planning trajectories; and,
displaying a second planar portion of said volumetric image data set collinear with a second set of said virtual needle linear planning trajectories and orthogonal with said major plane of said guide lattice device and with said first planar portion of the volumetric image data set.

8. The method according to claim 6 further including the step of adjusting a length of a selected first one of said plurality of a virtual needle planning trajectories to extend through said volumetric image data set from a first virtual needle end point in the volumetric image data set to a second virtual needle end point in the volumetric image data set.

9. The method according to claim 8 wherein the display step includes:
displaying a first planar portion of said volumetric image data set co-planar with a major plane of the guide lattice device, the first planar portion of the volumetric image data set corresponding to a physical position of the guide lattice relative to said area of said patient;
displaying a second planar portion of said volumetric image data set parallel with said major plane of the guide lattice, the second planar portion of the volumetric image data set being coincidence with a position of said selected first one of said plurality of virtual needle planning trajectories during adjusting of said length of the selected first one of the plurality of virtual needle planning trajectories to move from said first virtual needle end point to said second virtual needle end point;
displaying a third planar portion of said volumetric image data set orthogonal with a major plane of said guide lattice device and collinear with said selected first one of said plurality of virtual needle planning trajectories; and,
displaying a fourth planar portion of said volumetric image data set collinear with said selected first one of said plurality of virtual needle planning trajectories and orthogonal with said major plane of said guide lattice device and with said third planar portion of the volumetric image data set.

10. An apparatus for planning a surgical procedure for inserting a plurality of objects into a patient along a plurality of surgical planning trajectories from a plurality of entry points on the patient to a plurality of target points within the patient, the apparatus comprising:
an imaging device generating an image volume data set of an area of a patient to be treated;
a multi-apertured surgical planning grid lattice movable relative to the imaging device to a first position relative to the patient for defining a plurality of linear planning trajectories extending from the planning grid lattice and through the patient; and,
a display device for displaying said image volume data set of said area of said patient with a virtual representation of said grid lattice superimposed on the image volume data set to provide a visual image of a position of the grid lattice relative to anatomy of said patient.

11. The apparatus according to claim 10 wherein the display device includes:
means for displaying a first planar portion of said image volume data set coplanar with a major plane of the grid lattice, the first planar portion of the image volume data set corresponding to a physical position of the grid lattice relative to said area of said patient;
means for displaying a second planar portion of the image volume data set orthogonal with said major plane of the grid lattice, the second planar portion of the image volume data set corresponding to a first cross-section view of said area of said patient with a first cross-sectional virtual representation of the grid lattice superimposed on the image volume data set; and,
means for displaying a third planar portion of the image volume data set orthogonal with said major plane of the grid lattice and orthogonal with said second planar portion, the third planar portion of the image volume data set corresponding to a second cross-sectional view of said area of said patient with a second cross-sectional virtual representation of the grid lattice superimposed on the image volume data set.

12. The apparatus according to claim 11 wherein the first device is an imaging device adapted to scan said area of the patient and generate said image volume data set.

13. The apparatus according to claim 10 further including:
localizing means for determining a position of the grid lattice relative to the image volume data set, the display device being responsive to the localizing means for displaying said image volume data set of said area of said patient with said virtual representation of said grid lattice superimposed on the image volume data set to provide said visual representation of the position of the grid lattice relative to said anatomy of said patient.

14. The apparatus according to claim 13 wherein:

the first device is an imaging device adapted to scan said area of the patient and generate said image volume data set; and, the localizing means includes a mechanical arm assembly mounted on a first end in a fixed relationship to said imaging device and carrying said grid lattice on a second free end thereof, the mechanical arm assembly being selectively movable to selectively hold the grid lattice in a plurality of positions relative to said patient to be treated.

15. The apparatus according to claim 14 wherein the display device includes means for selectively updating said display of said area of said patient to display virtual representations of said grid lattice superimposed on the image volume data set for each of said plurality of positions of said grid lattice relative to said patient to be treated.

16. The apparatus according to claim 10 wherein:

the grid lattice is a multi-apertured surgical planning guide lattice device defining a first virtual needle linear planning trajectory extending through the image volume data set from a first aperture to a first virtual needle end point in the image volume data set; and, the apparatus includes means for adjusting a length of said first virtual needle linear planning trajectory to extend through said image volume data set from the multi-apertured surgical planning guide lattice device to a second virtual needle end point in the image volume data.

17. The apparatus according to claim 16 wherein the display device includes:

means for displaying a first planar portion of said image volume data set coplanar with a major plane of the guide lattice device, the first planar portion of the image volume data set corresponding to a physical position of the guide lattice device relative to said area of said patient; and, means for displaying a second planar portion of said image volume data set parallel with said major plane of the guide lattice device, the second planar portion of the image volume data set being coincident with said position of said first virtual needle end point during said adjusting of said length of said first virtual needle planning trajectory to move from said first virtual needle end point to said second virtual needle end point.

18. The apparatus according to claim 16 wherein:

the multi-apertured surgical planning guide lattice device defines a plurality of virtual needle planning trajectories extending through said image volume data set from a corresponding plurality of apertures formed by the guide lattice device to a corresponding plurality of virtual needle end points in the image volume data set;

the display device is adapted to display a first planar portion of said image volume data set orthogonal with a major plane of said guide lattice device and collinear with a first set of said plurality of virtual needle planning trajectories; and, the display device is adapted to display a second planar portion of said image volume data set orthogonal with a major plane of said guide lattice device and collinear with a second set of said plurality of virtual needle planning trajectories.

* * * * *

UNITED STATES PATENT AND TRADEMARK OFFICE
CERTIFICATE OF CORRECTION

PATENT NO.   : 6,366,796 B1
DATED        : April 2, 2002
INVENTOR(S)  : Yanof et al.

It is certified that error appears in the above-identified patent and that said Letters Patent is hereby corrected as shown below:

<u>Title page,</u>
Please correct the listing of the Inventors as follows:

-- [75] Inventors: Jeffrey H. Yanof, Solon; Kenneth L. Freeman, Stow, both of OH (US); Barry L. Werner, Chesterbrook, PA (US). --

Signed and Sealed this

Seventeenth Day of September, 2002

*Attest:*

*Attesting Officer*

JAMES E. ROGAN
*Director of the United States Patent and Trademark Office*